US00PP20602P2

(12) United States Plant Patent
Talago

(10) Patent No.: US PP20,602 P2
(45) Date of Patent: Dec. 22, 2009

(54) ***BARBERRY* PLANT NAMED 'TALAGO'**

(50) Latin Name: *Berberis thunbergii*
Varietal Denomination: Talago

(75) Inventor: Stanley Talago, Grafton, WV (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/287,024

(22) Filed: Oct. 1, 2008

(51) Int. Cl.
*A01H 5/00* (2006.01)

(52) U.S. Cl. ..... Plt./241

(58) Field of Classification Search ..... Plt./241
See application file for complete search history.

*Primary Examiner*—Susan B McCormick Ewoldt
(74) *Attorney, Agent, or Firm*—C. A. Whealy

(57) ABSTRACT

A new and distinct cultivar of *Barberry* plant named 'Talago', characterized by its compact, low mounding and outwardly spreading plant habit; freely branching habit; dense and bushy growth habit; leaves that are initially orange red in color and become bright yellow in color with development; and leaves that have good resistance to sunburn.

1 Drawing Sheet

Botanical designation: *Berberis thunbergii.*
Cultivar denomination: 'Talago'.

BACKGROUND OF THE INVENTION

The present invention relates to a new and distinct cultivar of *Barberry,* botanically known as *Berberis thunbergii* and hereinafter referred to by the name 'Talago'.

The new *Barberry* is a product of a planned breeding program conducted by the Inventor in Flemington, W. Va. The objective of the breeding program was to develop new compact and uniform *Barberries* with yellow-colored leaves that are resistant to sunburn.

The new *Barberry* originated from a cross-pollination during the spring of 1993 *Barberry thunbergii* 'Aurea', not patented, as the female, or seed parent and *Barberry thunbergii* 'Crimson Pygmy', not patented as the male, or pollen, parent. The new *Barberry* was discovered and selected by the Inventor in 1995 as a single plant within the progeny of the stated cross-pollination in a controlled environment in Flemington, W. Va.

Asexual reproduction of the new *Barberry* plant by softwood cuttings in a controlled greenhouse environment in Flemington, W. Va. since the June, 1999 has shown that the unique features of this new *Barberry* plant are stable and reproduced true to type in successive generations of asexual reproduction.

SUMMARY OF THE INVENTION

Plants of the new *Barberry* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Talago'. These characteristics in combination distinguish 'Talago' as a new and distinct cultivar of *Barberry:*

1. Compact, low mounding and outwardly spreading plant habit.

2. Freely branching habit; dense and bushy growth habit.
3. Leaves that are initially orange red in color and become bright yellow in color with development.
4. Leaves that have good resistance to sunburn.

Plants of the new *Barberry* can be compared to plants of the female parent, 'Aurea'. Plants of the new *Barberry* differ from plants of 'Aurea' in the following characteristics:

1. Plants of the new *Barberry* are more compact than plants of 'Aurea'.
2. Plants of the new *Barberry* are more mounding than plants of 'Aurea'.
3. Plants of the new *Barberry* are more resistant to sunburn than plants of 'Aurea'.

Plants of the new *Barberry* can be compared to plants of the male parent, 'Crimson Pygmy'. Plants of the new *Barberry* differ from plants of 'Crimson Pygmy' in the following characteristics:

1. Plants of the new *Barberry* are more compact than plants of 'Crimson Pygmy'.
2. Developing leaves of plants of the new *Barberry* are orange red in color whereas developing leaves of plants of 'Crimson Pygmy' are burgundy in color.
3. Fully expanded leaves of plants of the new *Barberry* are bright yellow in color whereas fully expanded leaves of plants of 'Crimson Pygmy' are burgundy in color.

Plants of the new *Barberry* can be compared to plants of the *Berberis thunbergii* 'Aurea Nana', not patented. In side-by-side comparisons conducted in Flemington, W. Va., plants of the new *Barberry* differed from plants of 'Aurea Nana' in the following characteristics:

1. Plants of the new *Barberry* were more compact than plants of 'Aurea Nana'.
2. Plants of the new *Barberry* were more mounding than plants of 'Aurea Nana'.
3. Plants of the new *Barberry* had shorter internodes than plants of 'Aurea Nana'.
4. Plants of the new *Barberry* had smaller leaves than plants of 'Aurea Nana'.
5. Plants of the new *Barberry* were more resistant to sunburn than plants of 'Aurea Nana'.

Plants of the new *Barberry* can also be compared to plants of the *Barberry thunbergii* 'Monlers', disclosed in U.S. Plant Pat. No. 9,577. In side-by-side comparisons conducted in Flemington, W. Va., plants of the new *Barberry* differed from plants of 'Monlers' in the following characteristics:

1. Plants of the new *Barberry* were more compact than plants of 'Monlers'.
2. Plants of the new *Barberry* were more mounding than plants of 'Monlers'.
3. Plants of the new *Barberry* had shorter internodes than plants of 'Monlers'.
4. Plants of the new *Barberry* had shorter leaves than plants of 'Monlers'.

BRIEF DESCRIPTION OF THE PHOTOGRAPHS

The accompanying colored photographs illustrate the overall appearance of the new *Barberry,* showing the colors as true as it is reasonably possible to obtain in colored reproductions of this type. Colors in the photographs may differ slightly from the color values cited in the detailed botanical description which accurately describe the colors of the new *Barberry.*

The photograph at the top of the sheet is a side perspective view of a typical plant of 'Talago' grown in an outdoor nursery.

The photograph at the bottom of the sheet is a close-up view of typical leaves of 'Talago'.

DETAILED BOTANICAL DESCRIPTION

The aforementioned photographs and following observations, measurements and values describe plants grown in Grand Haven, Mich. during the spring to autumn in an outdoor nursery and under conditions which closely approximate commercial production. Plants had been growing for five years when the photographs and the description were taken. In the description, color references are made to The Royal Horticultural Society Colour Chart, 1995 Edition, except where general terms of ordinary dictionary significance are used.

Botanical classification: *Berberis thunbergii* 'Talago'.

Parentage:

*Female, or seed, parent.*—*Barberry thunbergii* 'Aurea', not patented.

*Male, or pollen, parent.*—*Barberry thunbergii* 'Crimson Pygmy', not patented.

Propagation:

*Type.*—By softwood cuttings.

*Time to initiate roots.*—About 25 days at 24° C.

*Time to produce a rooted young plant.*—About six months at 24° C.

*Root description.*—Fine, fibrous; yellow-green to brown in color.

*Rooting habit.*—Freely branching; dense.

Plant description:

*Plant form and growth habit.*—Perennial shrub. Compact, low mounding and outwardly spreading plant habit; moderately vigorous growth habit.

*Branching habit.*—Freely branching habit, dense and bushy growth habit, lateral branches potentially forming at every node; pinching is typically not required.

*Plant height.*—About 20 cm.

*Plant diameter* (*area of spread*).—About 47 cm.

Lateral branch description:

*Length.*—About 15 cm.

*Diameter.*—About 2 mm to 3 mm.

*Internode length.*—About 4 mm to 5 mm.

*Aspect.*—About 30° to 45° from vertical.

*Texture.*—Smooth, glabrous.

*Color, young.*—Close to 144B.

*Color, fully developed.*—Close to 177A.

*Thorns.*—Quantity/arrangement: About one at each node. Length: About 5 mm. Width: About 0.5 mm. Color, young: Close to 144B. Color, fully developed: Close to 177A.

Foliage description:

*Arrangement.*—Alternate, simple.

*Length.*—About 1.7 cm.

*Width.*—About 1.1 cm.

*Shape.*—Spatulate.

*Apex.*—Obtuse.

*Base.*—Attenuate.

*Margin.*—Entire.

*Texture, upper and lower surfaces.*—Smooth, glabrous.

*Venation pattern.*—Pinnate.

*Color.*—Developing leaves, upper and lower surfaces: Close to 33A tinted with close to 151B. Fully expanded leaves, upper and lower surfaces: Close to 151C; in the shade, tinted with close to 144B; venation, similar to surface color.

*Petiole.*—Length: About 4 mm. Diameter: About 1 mm. Texture, upper and lower surfaces: Smooth, glabrous. Color, upper and lower surfaces: Close to 151A; in the shade, tinted with close to 144B.

Flower description: Flower development has not been observed on plants of the new *Barberry.* Seeds/fruits: Seed and fruit development have not been observed on plants of the new *Barberry* plant.

Garden performance: Plants of the new *Barberry* have been observed to have excellent garden performance and to tolerate rain, wind and temperatures ranging from about −27° C. to about 37° C.

Pathogen/pest resistance: Plants of the new *Barberry* have not been shown to be resistant to pathogens and pests common to *Barberry.*

It is claimed:

1. A new and distinct *Barberry* plant named 'Talago,' as illustrated and described.

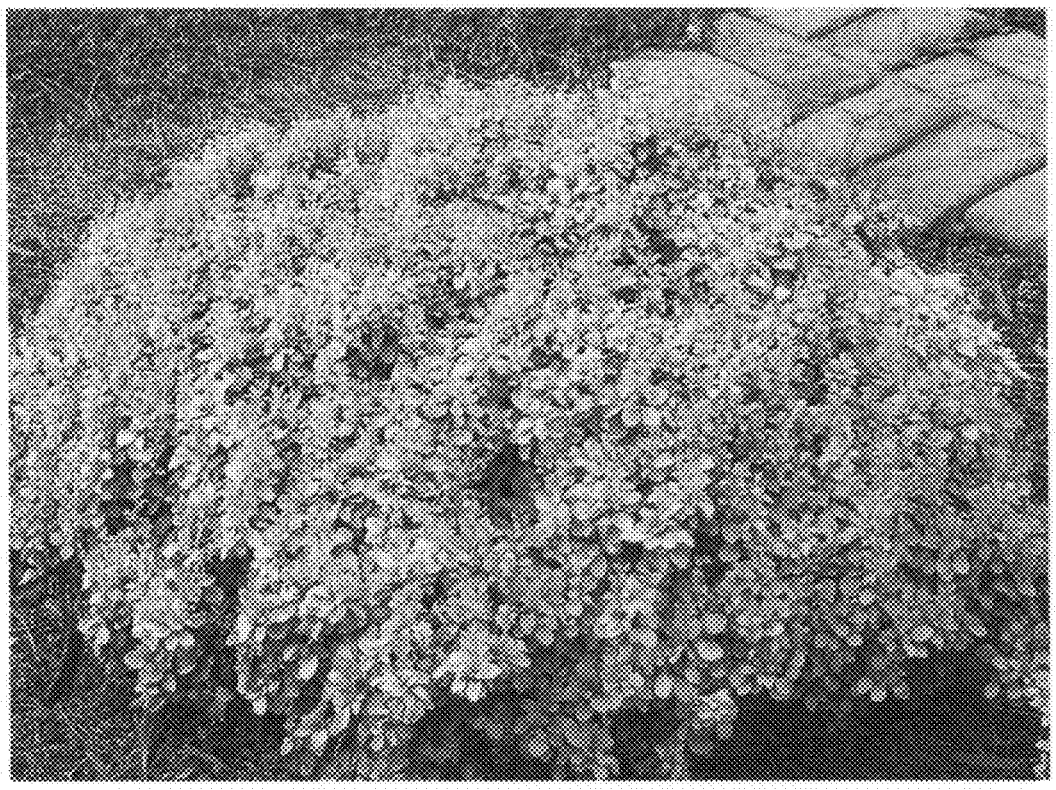
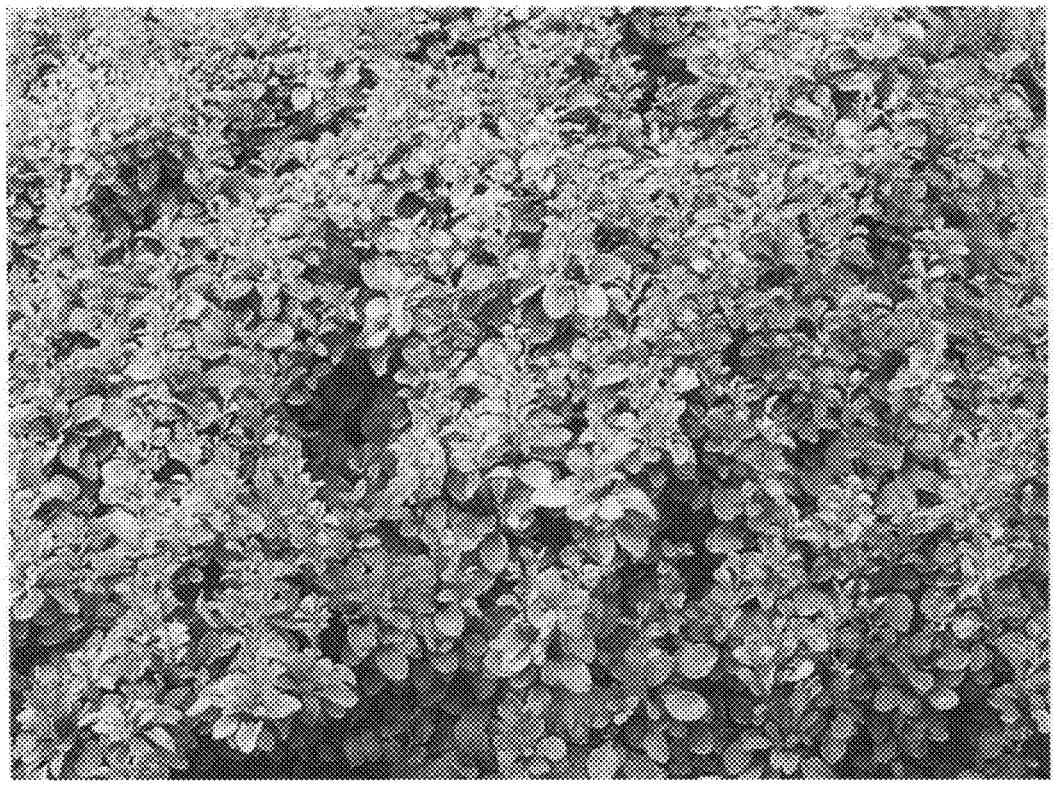

* * * * *